US010683465B2

(12) United States Patent
Borsotti et al.

(10) Patent No.: US 10,683,465 B2
(45) Date of Patent: Jun. 16, 2020

(54) PROCESS FOR THE SELECTIVE HYDROGENATION OF VEGETABLE OILS USING EGG-SHELL TYPE CATALYSTS

(71) Applicant: NOVAMONT S.P.A., Novara (IT)

(72) Inventors: Giampietro Borsotti, Novara (IT); Francesca Digioia, Barengo (IT)

(73) Assignee: NOVAMONT S.P.A., Novara (IT)

( * ) Notice: Subject to any disclaimer, the term of this patent is extended or adjusted under 35 U.S.C. 154(b) by 0 days.

(21) Appl. No.: 16/310,602

(22) PCT Filed: Jun. 20, 2017

(86) PCT No.: PCT/EP2017/065017
§ 371 (c)(1),
(2) Date: Dec. 17, 2018

(87) PCT Pub. No.: WO2017/220532
PCT Pub. Date: Dec. 28, 2017

(65) Prior Publication Data
US 2019/0249113 A1  Aug. 15, 2019

(30) Foreign Application Priority Data
Jun. 21, 2016 (IT) .................. 102016000063875

(51) Int. Cl.
| | | |
|---|---|---|
| *C11C 3/12* | (2006.01) | |
| *B01J 35/00* | (2006.01) | |
| *C07C 67/303* | (2006.01) | |
| *B01J 21/18* | (2006.01) | |
| *B01J 23/44* | (2006.01) | |
| *B01J 23/38* | (2006.01) | |
| *B01J 23/70* | (2006.01) | |
| *B01J 23/16* | (2006.01) | |

(52) U.S. Cl.
CPC .............. *C11C 3/126* (2013.01); *B01J 21/18* (2013.01); *B01J 23/44* (2013.01); *B01J 35/008* (2013.01); *C07C 67/303* (2013.01); *C11C 3/12* (2013.01); *B01J 23/16* (2013.01); *B01J 23/38* (2013.01); *B01J 23/70* (2013.01)

(58) Field of Classification Search
CPC ... C11C 3/12; C11C 3/126; B01J 23/44; B01J 35/008; B01J 23/16; B01J 23/38; B01J 23/70; C07C 67/303
See application file for complete search history.

(56) References Cited

U.S. PATENT DOCUMENTS

| 4,519,951 A * | 5/1985 | Qualeatti ................ B01J 23/40 554/144 |
| 8,536,236 B2 * | 9/2013 | Lok ......................... B01J 21/04 502/162 |

FOREIGN PATENT DOCUMENTS

| WO | WO-2011/080296 A1 | 7/2011 | |
| WO | 2016/102509 | * 6/2016 | ............... C11C 3/12 |

OTHER PUBLICATIONS

Khajavi et al: "Shape and Transition State Selective Hydrogenations Using Egg-Shell Pt-MIL-101(Cr) Catalyst", ACS Catalysis, vol. 3, No. 11, Oct. 2, 2013 (Oct. 2, 2013), pp. 2617-2626, XP055337337.
Simakova et al: "Hydrogenation of Vegetable Oils over Pd on Nanocomposite Carbon Catalysts", Industrial & Engineering Chemistry Research., vol. 47, No. 19, Aug. 23, 2008 (Aug. 23, 2008), pp. 7219-7225, XP055337319.
Fritsch et al: "Development of catalytically reactive porous membranes for the selective hydrogenation of sunflower oil", Catalysis Today, Elsevier, Amsterdam, NL, vol. 118, No. 1-2, Oct. 30, 2006 (Oct. 30, 2006), pp. 121-127, XP027976234.
Santana et al: "Vegetable fat hydrogenation in supercritical-fluid solvents: Melting behavior analysis by DSC and NMR", The Journal of Supercritical Fluids, Elsevier, Amsterdam, NL, vol. 46, No. 3, Oct. 1, 2008 (Oct. 1, 2008), pp. 322-328, XP023976688.
Santana et al: "Sunflower oil hydrogenation on Pd in supercritical solvents: Kinetics and selectivities", The Journal of Supercritical Fluids, Elsevier, Amsterdam, NL, vol. 41, No. 3, May 3, 2007 (May 3, 2007), pp. 391-403, XP022054908.

* cited by examiner

*Primary Examiner* — Yate' K Cutliff
(74) *Attorney, Agent, or Firm* — Polsinelli PC

(57) ABSTRACT

The invention relates to a process for the hydrogenation of vegetable oils that selectively converts polyunsaturated fatty acids into mono-unsaturated fatty acids, and to the products obtained therefrom. Vegetable oils obtained by the process according to the invention have a particularly high content of monounsaturated fatty acids and are suitable for use as raw materials for the synthesis of chemical intermediates.

20 Claims, No Drawings

PROCESS FOR THE SELECTIVE HYDROGENATION OF VEGETABLE OILS USING EGG-SHELL TYPE CATALYSTS

CROSS REFERENCE TO RELATED APPLICATIONS

This application is the National Phase of Application No. PCT/EP2017/065017 filed Jun. 20, 2017, which claims priority to application Ser. No. 102016000063875 filed in Italy on Jun. 21, 2016 under 35 U.S.C. § 119. The entire contents of each application are hereby incorporated by reference.

The present invention relates to a process for the selective hydrogenation of vegetable oils. In particular this invention relates to a process for the hydrogenation of vegetable oils which is capable of selectively converting polyunsaturated fatty acids into mono-unsaturated fatty acids and the products obtained therefrom. The vegetable oils obtained by the process according to the invention have in particular a high mono-unsaturated fatty acids content and are particularly suitable for use as raw materials for the synthesis of chemical intermediates. Vegetable oils are now an important raw material for the chemical industry on account of the increasingly pressing need to identify raw materials of renewable origin which are alternatives to conventional oil-based sources.

For example WO2008/138892 describes a process of oxidative cleavage which, starting from vegetable oils containing mono-unsaturated fatty acid triglycerides, makes it possible to produce intermediates which are important for the preparation of polyesters, such as for example the saturated dicarboxylic acids azelaic acid or brassylic acid.

As is known, vegetable oils comprise mixtures of fatty acid triglycerides. These fatty acids generally contain from 16 to 22 carbon atoms and may be saturated, for example stearic acid, mono-unsaturated, for example oleic acid, or polyunsaturated, such as for example linoleic acid and linolenic acid.

These vegetable oils have quite different compositions, depending upon the nature of the plant species from which they are obtained, for example different types and contents of mono-unsaturated fatty acids. This constitutes an appreciable limitation on the use of vegetable oils as raw materials for the organic chemical industry.

It has therefore become necessary to find and make use of processes to modify the composition of vegetable oils in order to encourage their use in this sector.

For example, hydrogenation processes have wide application in the chemical field, and in particular in the field of oil chemistry. The double bonds present in the chains of unsaturated fatty acids can in fact be saturated by the addition of hydrogen in the presence of catalysts such as for example nickel, platinum, palladium or copper.

The hydrogenation processes are exothermic and the reaction rate depends on the type of oil, the temperature, the activity and concentration of the catalyst, and the hydrogen pressure.

Although widely used, these processes nevertheless have appreciable limitations from the point of view of selectivity. In particular the possibility of maintaining high conversions of polyunsaturated fatty acids while avoiding the formation of saturated fatty acids is limited.

A system for increasing the selectivity is that of increasing the reaction temperature. However this may result in the occurrence of isomerization reactions of the unsaturated fatty acids present in the vegetable oil.

There is therefore a need to develop new selective hydrogenation processes for vegetable oils capable of selectively converting polyunsaturated fatty acids into monounsaturated fatty acids.

Starting from this problem it has now surprisingly been discovered that through operating in the presence of a supported metal catalyst with an active phase distribution of the egg-shell type it is possible to obtain significant conversion of the polyunsaturated fatty acids of the triglycerides present in the oil, even at low temperatures, while at the same time increasing or at least maintaining selectivity for monounsaturated fatty acids. These advantageous effects can be achieved even when operating with small quantities of catalyst, at atmospheric pressure or a pressure a little above atmospheric. The said process can also be effectively performed when water is both present and absent.

In particular this invention relates to a process for the catalytic hydrogenation of vegetable oils in which the oil is placed in contact with molecular hydrogen in the presence of a supported metal catalyst of the egg-shell type, i.e. one in which the active phase is mainly distributed on the outer surface of the support, at a temperature which is advantageously less than or equal to 50° C., preferably less than or equal to 25° C., and more preferably less than or equal to 20° C.

It has in fact surprisingly been discovered that operating under these conditions it is possible to improve the catalytic activity and selectivity of metal catalysts as regards hydrogenation of the polyunsaturated fatty acids of the triglycerides present in the oil.

Catalysts of the egg-shell type comprising palladium metal, preferably supported on carbon or alumina, are particularly suitable for this purpose.

Thanks to the process according to this invention it is in fact possible to achieve selective conversion of the polyunsaturated fatty acids into monounsaturated fatty acids and obtain oil with a high monounsaturated fatty acids content that is particularly suitable for subsequent use as a starting material for the synthesis of chemical intermediates.

As a result of this composition, the vegetable oil obtained from the process according to the invention is particularly suitable for being used as a starting material, also mixed with other vegetable oils, for oxidative scission processes in which inorganic and organic peroxides, peracids, nitric acid, permanganates, periodates, O2, O3 or gaseous mixtures thereof are used as oxidizing agents.

Oxidative scission processes which use peroxides, such as hydrogen peroxide, and O2 or mixtures containing O2 as oxidizing agents are preferred. Specific examples are the oxidative scission processes described in the applications WO 2008/138892, WO 2011/080296 or WO 2013/079849 A1.

A particularly advantageous feature of the oil obtained by the process of the present invention is the content of various positional isomers of monounsaturated fatty acids. These are useful e.g. for the preparation of bifunctional molecules of various chain lengths, starting from renewable resources. For example, the catalytic hydrogenation of a vegetable oil rich in polyunsaturated C18 fatty acids according to this process allows to obtain significant amounts of 12-octadecencarboxylic acid (C18:1 (n-6)), which in turn can be subjected to one of the above mentioned oxidative cleavage processes to obtain renewable C12 dicarboxylic acids. The vegetable oil obtained from the process according to the present invention is particularly useful as a starting material for oxidative scission processes comprising the steps of:

a) reacting the triglycerides of unsaturated carboxylic acids with an oxidizing compound, preferably in the presence of a catalyst able to catalyze the oxidation reaction of the olefinic double bond, obtaining an intermediate compound containing vicinal diols;

b) reacting said intermediate compound with oxygen, or a gaseous mixture containing oxygen, preferably in the presence of a catalyst able to catalyze the oxidation reaction of the vicinal diols to carboxyl groups, obtaining saturated monocarboxylic acids and triglycerides containing saturated dicarboxylic acids.

When the vegetable oil obtained from the process according to the present invention is used as a raw material for oxidative scission processes in mixtures with other vegetable oils, preferably said mixtures contain more than 10% of the vegetable oil obtained from the process of the present invention.

When present, the quantity of water during the reaction may vary, preferably remaining at 400:1 or less, more preferably 200:1 or less, even more preferably 100:1 or less with respect to the weight of the metal catalyst. Water may be present from the start of the reaction or may be introduced progressively during the course of it, for example by saturating specific quantities of hydrogen gas.

Advantageously no water other than that present in the catalyst is added.

According to one aspect of this invention water is absent in the course of the reaction.

The process according to this invention can hydrogenate vegetable oils such as soya oil, olive oil, castor oil, sunflower oil, peanut oil, maize oil, palm oil, jatropha oil, thistle oil such as that from *Cynara cardunculus, Silybum marianum*, safflower oil, cuphea oil, Brassicaceae oils such as those from *Crambe abyssinica, Brassica carinata, Brassica napus* (colza), Lesquerella, or mixtures thereof. Waste frying oils or other spent vegetable oils may also be hydrogenated according to this invention.

The use of sunflower oil, Brassicaceae oils or thistle oil such as that from *Cynara cardunculus* and *Silybum marianum* is particularly preferred.

In particular the latter are obtained from plant species belonging to the Cardueae tribe and are very robust annual or perennial herbaceous plants which also have the further advantage that they can be cultivated in arid areas of not very favourable climate.

The catalyst for the process according to this invention, comprising a supported metal catalyst, can be used in the form of sheets, particles, cylindrical granules or spheres of dimensions of typically between 2 and 4 mm.

Examples of metal catalysts which can be used are nickel, platinum, palladium, copper, iron, rhodium, ruthenium, iridium, osmium, molybdenum, tungsten and mixtures thereof.

According to a preferred aspect of the invention the metal catalyst used comprises palladium, in a quantity generally of between 20 mg/kg and 500 mg/kg, preferably between 30 and 100 mg/kg, and more preferably between 40 and 50 mg/kg with respect to the quantity of vegetable oil which has to be hydrogenated. Catalyst quantities may vary within this range depending upon the form of the catalyst, its surface area and the concentration of metal catalyst with respect to any support. Typically the catalyst comprises 0.1-10% by weight of palladium metal; preferably the catalyst comprises 0.1-5% by weight and more preferably 0.1-0.5% by weight of palladium metal.

The metal present in the catalyst is supported on any support known in the art, for example on alumina, carbon in various forms, including nanotubes, metal oxides such as $CeO_2$, $ZrO_2$, $CrO_2$, $TiO_2$, MgO, silica, inorganic-organic sol-gel matrices, polycrystalline oxide substrates, amorphous carbon, zeolites, aluminosilicates, alkaline earth carbonates such as magnesium carbonate, calcium carbonate or barium carbonate, barium sulphate, montmorillonites, polymer matrices, multifunctional resins, ion exchange resins, ceramic supports or mixtures of two or more of these. In a preferred form of the process, the catalyst comprises palladium metal supported on alumina or carbon.

The supported catalyst may be prepared according to techniques known to those skilled in the art, for example by finely dispersing a metal salt on the support and subsequently reducing the metal salt to the metallic state. The stage of dispersion of the metal salt may for example be performed through impregnation, adsorption from a solution, co-precipitation or deposition, for example by means of chemical vapour deposition. The stage of reducing the metal salt is typically performed by heating the supported metal salt in the presence of a molecular hydrogen atmosphere. The catalyst preparation stage may be carried out separately from the hydrogenation process according to this invention or may take place in a preliminary stage of it. For example the supported metal salt may be placed in the hydrogenation reactor and reduced in situ in a hydrogen atmosphere before the vegetable oil is added. Particularly suitable catalysts for use in the process according to this invention are for example palladium of the egg-shell type on carbon with 5% by weight of palladium (e.g. as manufactured by Johnson Matthey), or 0.3% by weight.

In this application, catalysts of the "egg-shell" type are intended to be catalysts whose active metal component or one or more of its precursors are mainly (for example at least 50%) located as an outer layer on the surface of the support and are not dispersed within the support.

Catalysts of the egg-shell type may comprise between approximately 0.1% and approximately 10% by weight, advantageously between approximately 0.2% and 5% by weight of the metal component, expressed as a nominal percentage by weight of the metal component converted into the metallic state if not already all in the metallic state, on the basis of the weight of the egg-shell catalyst.

Advantageously more than 50%, for example more than 60% or more advantageously more than 80%, of the metal component is located in the peripheral outer layer of the support. Egg-shell palladium-based catalysts supported on carbon or γ-alumina are advantageously used.

Advantageously the catalyst is recovered at the end of the reaction and recycled to subsequent hydrogenation reactions.

Among the advantages of the process according to the present invention there is the fact that it may be conducted in particular in the presence of palladium-based catalysts, without the need to add to the catalyst promoters for improving the selectivity, such as copper, silver, zinc, tin, lead, titanium, zirconium, hafnium, vanadium, niobium, tantalum, chromium, molybdenum, tungsten or manganese.

In general, the process according to this invention may be carried out in one or more suitable items of equipment capable of ensuring suitable mass/liquid/solid mixing, such as for example stirred reactors, fixed bed reactors, moving bed reactors, fluidised bed and air lift reactors.

At the end of the reaction, the catalyst may be easily recovered by means of known techniques and reused several times. In a preferred embodiment, the process for catalytic hydrogenation of vegetable oils according to the present invention comprises a step during which the catalyst is separated from the vegetable oil, for example by means of filtration or decantation.

In the case of stirred reactors, in particular, stirring of the means helps determine the speed of diffusion of the hydrogen and the degree of contact between the vegetable oil and hydrogen.

Depending on the volume and the configuration of the reactor, stirring speeds ranging for example between 100 and 1200 rpm, more particularly between 200 and 1000 rpm, may be used.

The stirring speed of the system is preferably between 500 and 1000 rpm.

The hydrogenation reaction is carried out at temperatures of 50° C. or below, preferably between 30° C. and 0° C. and even more preferably between 25° C. and 0° C., even more preferably below 20° C. and above 0° C., for example between 3° C. and 18° C. At higher temperatures, a greater degree of cis-trans isomerization of the unsaturated acids has been observed, leading to the formation of considerable amounts of trans isomers.

In general the trans isomers have higher melting points than the cis isomers and beyond particular levels of conversion this can give rise to the formation of a solid phase which for example contains trans 9-octadecenoic acid. When compared to naturally occurring vegetable oils (containing mainly cis isomers), the vegetable oils containing trans isomers are also less susceptible to oxidation reactions by peroxides. This determines longer reaction times when said oils are subjected to oxidative cleavage reactions.

The temperature may be adjusted for example by heating the reaction mixture before the start of the reaction. Because the hydrogenation reaction is exothermic, progress of the reaction gives rise to a gradual increase in temperature within the reaction mixture. The said increase is typically controlled through cooling systems preventing excessive heating, which might have an adverse effect on the course of the reaction.

As far as the molecular hydrogen is concerned, the hydrogenation reaction is typically performed at molecular hydrogen pressures of between 1 and 15 bar, preferably between 1 and 10 bar, more preferably between 1 and 6 bar, maintaining the total pressure below 20 bar, preferably below 15 bar and more preferably below 10 bar. Depending upon requirements, hydrogen may be introduced into the reactor continuously, adjusting the flow, or fed in as one or more aliquots, for example 3, 5 or 7 aliquots, while maintaining the hydrogen pressure within the range indicated above.

The process is advantageously performed in the presence of organic solvents, preferably selected from hydrocarbons, preferably hydrocarbons with a chain length higher than C5, esters, ketones, for example C3-C8 ketones, C3-C6 alcohols, or ethers such as for example THF, to reduce the viscosity of the system and increase the reaction rate. Those skilled in the art will readily be able to select the most suitable solvent from these on the basis of the solubility of the oil which has to be hydrogenated and the presence of water in the reaction mixture. Preferred organic solvents are those which can easily be recovered, for example by distillation. Specific examples of suitable organic solvents are petroleum ether, hexane, heptane, octane, acetone, ethyl acetate, toluene, isobutanol, methyl ethyl ketone, methyl isobutyl ketone.

The weight ratio between the organic solvent and the oil is preferably between 0.25:1 and 3:1, more preferably between 0.5:1 and 2:1.

Additives such as bases can be added in order to further improve the selectivity of the hydrogenation reaction as known in the art. Examples of said bases are amines, oxides, hydroxydes, or carbonates of alkali metals, alkaline earth metals or ammonium. Specific examples of bases are N-ethyldiisopropylamine, triethylamine, diamines such as ethylenediamine, its homologues and/or derivatives such as tetramethylethylenediamine, tetraalkyl amines, where the alkyl chain are for example C2 to C6 alkyl chains, cyclic amines such as diazabicyclooctane or diazabicycloundecene, ammonium hydroxide salts such as choline or tetrabutylammonium hydroxide. Choline or tetrabutylammonium hydroxide are advantageously used in the presence of a co-solvent such as methanol when petroleum ether is used as solvent for the vegetable oil. In this case the methanol solubilizes the tetrabutylammonium hydroxide and forms a separated phase in which the catalyst will partition at the end of the reaction, facilitating the recovery.

The process can be controlled in a manner known to those skilled in the art, for example by measuring the pressure within the reactor and interrupting the reaction when a specific quantity of hydrogen has been absorbed.

As an alternative the course of the reaction can be monitored by sampling and analysing the composition of the reaction mixture. The theoretical amount of hydrogen required for the completion of the reaction can be easily determined on the basis of the composition of the starting vegetable oil for example by analyzing the amount of unsaturations.

The duration of the process according to this invention depends on the nature of the vegetable oil, the operating conditions, the desired conversion, and the dimensions of the reactor used, and is typically from 5 minutes to 6 hours, for example from 60 to 300 minutes.

According to a preferred aspect, the hydrogenation reaction according to this invention is carried out at temperatures of between 0° C. and 30° C., more preferably between 0° C. and 25° C. and even more preferably between 0° C. and 20° C., preferably maintaining the molecular hydrogen pressure between 1 and 2 bar, more preferably between 1 and 1.5 bar.

According to a particularly preferred aspect the reaction is carried out at temperatures of between 18° C. and 3° C. Operating under these conditions it is in fact possible to achieve particularly high conversion of triglycerides of polyunsaturated acids and selectivity for monounsaturated acid triglycerides without any need for additives such as amines.

Carrying out the process at temperatures of 18° C. or below, an organic solvent is advantageously used because of the increased viscosity. This notwithstanding, this process requires limited quantities of organic solvent to achieve satisfactory conversion; for example solvent in a ratio of between 1:1 and 2:1 by weight with respect to the oil is advantageously used at these temperatures.

The invention will now be illustrated by a number of examples which are intended to be merely illustrative in scope and not limiting upon the invention.

EXAMPLES

In the following examples the carboxylic acid composition of the oil was determined after transesterification of an oil sample (140 µl) in 140 µl of methanolic KOH (2N). The methyl esters of the carboxylic acids were extracted from the methanolic solutions in 3 ml of hexane and then analyzed in a gas chromatograph equipped with flame ionization detector (FID) and a capillary column SLB-IL111 100 m×0.25 mm×0.2 micron (SUPELCO) at a constant pressure of 275 kPa.

Temperature programme of the oven: 100° C. (35 min)-2.5° C./min-140° C. (30 min)-5.0° C./min-260° C. (25 min) for a total time of 130 min.

Temperature of the injector: 250° C.; split ratio=250:1; carrier gas:helium.

The conversion of diunsaturated acids (C18:2) was determined as follows:

$$\frac{(\sum \text{starting C18:2} - \sum \text{final C18:2})}{\sum \text{starting C18:2}}$$

where Σ starting C18: and Σ final C18:2 correspond to the sum of the % weight of the various isomers of the diunsaturated C18 acids relative to the total carboxylic acid composition, before and after the hydrogenation reaction, respectively.

The selectivity with respect to the monounsaturated acids (C18:1) was determined as follows:

$$\frac{(\sum \text{final C18:1} - \sum \text{starting C18:1})}{(\sum \text{starting C18:2} - \sum \text{final C18:2})}$$

where Σ final C18:1 and Σ starting C18:1 correspond to the sum of the % weight of the various isomers of monounsaturated C18 acids relative to the total carboxylic acid composition, after and before the hydrogenation reaction, respectively, and Σ starting C18:2 and Σ final C18:2 correspond to the sum of the % weight of the various isomers of the diunsaturated C18 acids relative to the total carboxylic acid composition, before and after the hydrogenation reaction, respectively.

Example 1

The hydrogenation reaction was performed in a 500 ml cylindrical reactor fitted with an electromagnetic stirrer and a thermometer and connected to a hydrogen cylinder through a mass flowmeter.

The reactor was charged with 50 g of sunflower oil, approximately 110 ml of hexane and 0.05 g of powder catalyst comprising 5% Pd/C of the egg-shell type (Alfa & Aesar; dry).

The reactor was connected to a pump to remove air and then fed with a flow of $H_2$.

The reactor was vigorously stirred for 144 minutes at 700 rpm, holding the temperature at 15° C. in a cryostat. The quantity of hydrogen absorbed, equal to 2.1 L, was measured by means of a counter at the outlet from the reactor.

The catalyst was filtered and the organic solvent was evaporated off to obtain the hydrogenated sunflower oil. The percentage composition by weight of the C18 carboxylic acids in the hydrogenated oil in comparison with the total composition of carboxylic acids as measured by means of GC analysis after a reaction time of 144 minutes, in comparison with the composition of the starting oil, is shown in Table 1.

The conversion of linoleic acid was 80.5% and the selectivity for oleic acid was 93.3%.

TABLE 1

| Carboxylic acid composition | Sunflower oil | Example 1 | Example 2 (comparative) | Example 3 |
|---|---|---|---|---|
| Hydrogenation time | — | 144 min | 129 min | 214 min |
| C 18:0 | 3.3 | 6.7 | 11.6 | 6.3 |
| C 18:1 cis | 29.8 | 64.1 | 57.6 | 58.3 |
| C 18:1 trans | — | 10.6 | 9.3 | 22.3 |
| C 18:2 | 59.7 | 11.6 | 14.4 | 6.2 |
| C 18:3 | 0.2 | — | — | — |
| C18:2 conversion | — | 80.5% | 75.8% | 89.7% |
| C18:1 selectivity | — | 93.3% | 82.1% | 94.7% |

Example 2 (Comparative)

The hydrogenation reaction was performed as in Example 1, but using 0.05 g of powder catalyst comprising 5% non-egg-shell Pd/C (Aldrich; dry support).

The reactor was stopped after 129 minutes; the quantity of hydrogen absorbed was 2.1 L.

The catalyst was filtered off and the organic solvent was evaporated off in order to obtain the hydrogenated sunflower oil.

As shown in Table 1, conversion to linoleic acid was only 75.8% while selectivity for oleic acid was 82.2%, i.e. more than 10% less than that obtained under the same conditions using the egg-shell type catalyst in Example 1.

Example 3

The hydrogenation reaction was carried out in the same reactor as Example 1, charged with 85 g of sunflower oil, approximately 100 ml of isobutanol, 300 mg of water and 90 mg of catalyst comprising 5% Pd/C of the egg-shell type (Johnson & Matthey; 50% humidity).

The reactor was vigorously stirred for 214 minutes at 700 rpm, maintaining a temperature of 16-17° C. The quantity of hydrogen absorbed was 2.15 L.

The catalyst was filtered off and the organic solvent was evaporated off in order to obtain the hydrogenated sunflower oil. The percentage composition by weight of C18 carboxylic acids in the hydrogenated oil after a reaction time of 214 minutes is shown in Table 1.

The conversion of linoleic acid was more than 89% and selectivity for oleic acid was 94.7%.

The invention claimed is:

1. A process for the catalytic hydrogenation of a vegetable oil comprising a mixture of triglycerides of fatty acids comprising polyunsaturated fatty acids in which the oil is placed in contact with molecular hydrogen in the presence of a supported metal catalyst, wherein the said catalyst is of the egg-shell type and the process is carried out at a molecular hydrogen pressure of between 1 and 15 bar at a temperature from 0° C. to 30° C., wherein said polyunsaturated fatty acids are selectively converted into monounsaturated fatty acids.

2. The process according to claim 1 in which the said metal catalyst is selected from the group comprising nickel, platinum, palladium, copper, iron, rhodium, ruthenium, molybdenum, osmium, iridium, tungsten and mixtures thereof.

3. The process according to claim 2, in which the metal catalyst comprises metallic palladium.

4. The process according to claim 3, in which the hydrogenation is carried out in the presence of 20 mg/kg-500 mg/kg of metallic palladium with respect to the quantity of vegetable oil.

5. The process according to claim 3, in which the metal catalyst comprises 0.1-10% by weight of palladium metal.

6. The process according to claim 1, in which the support for the metal catalyst is selected from the group comprising alumina, carbon, $CeO_2$, $ZrO_2$, $CrO_2$, $TiO_2$, MgO, silica, inorganic-organic sol-gel matrices, polycrystalline oxide substrates, amorphous carbon, zeolites, aluminosilicates, alkaline earth carbonates such as magnesium carbonate, calcium carbonate or barium carbonate, barium sulphate, montmorillonites, polymer matrices, multifunctional resins, ion exchange resins, ceramic supports or mixtures of two or more of these.

7. The process according to claim 6, in which the catalyst comprises metallic palladium supported on alumina or carbon.

8. The process according to claim 1, in which the temperature is comprised between 0° C. and 25° C.

9. The process according to claim 1 carried out in the presence of an organic solvent selected from the group comprising hydrocarbons, esters, ketones, C3-C6 alcohols, and ethers.

10. The process according to claim 9 in which the organic solvent is in a ratio of between 0.25:1 and 3:1 by weight with respect to the vegetable oil.

11. The process according to claim 1 carried out in the presence of a quantity of water of 400:1 or less with respect to the weight of metal catalyst.

12. The process according to claim 1 wherein the vegetable oil is selected from the group comprising sunflower oil, Brassicaceae oils or thistle oils.

13. The process according to claim 4, in which the metal catalyst comprises 0.1-10% by weight of palladium metal.

14. The process according to claim 2, in which the support for the metal catalyst is selected from the group comprising alumina, carbon, $CeO_2$, $ZrO_2$, $CrO_2$, $TiO_2$, MgO, silica, inorganic-organic sol-gel matrices, polycrystalline oxide substrates, amorphous carbon, zeolites, aluminosilicates, alkaline earth carbonates such as magnesium carbonate, calcium carbonate or barium carbonate, barium sulphate, montmorillonites, polymer matrices, multifunctional resins, ion exchange resins, ceramic supports or mixtures of two or more of these.

15. The process according to claim 3, in which the support for the metal catalyst is selected from the group comprising alumina, carbon, $CeO_2$, $ZrO_2$, $CrO_2$, $TiO_2$, MgO, silica, inorganic-organic sol-gel matrices, polycrystalline oxide substrates, amorphous carbon, zeolites, aluminosilicates, alkaline earth carbonates such as magnesium carbonate, calcium carbonate or barium carbonate, barium sulphate, montmorillonites, polymer matrices, multifunctional resins, ion exchange resins, ceramic supports or mixtures of two or more of these.

16. The process according to claim 4, in which the support for the metal catalyst is selected from the group comprising alumina, carbon, $CeO_2$, $ZrO_2$, $CrO_2$, $TiO_2$, MgO, silica, inorganic-organic sol-gel matrices, polycrystalline oxide substrates, amorphous carbon, zeolites, aluminosilicates, alkaline earth carbonates such as magnesium carbonate, calcium carbonate or barium carbonate, barium sulphate, montmorillonites, polymer matrices, multifunctional resins, ion exchange resins, ceramic supports or mixtures of two or more of these.

17. The process according to claim 5, in which the support for the metal catalyst is selected from the group comprising alumina, carbon, $CeO_2$, $ZrO_2$, $CrO_2$, $TiO_2$, MgO, silica, inorganic-organic sol-gel matrices, polycrystalline oxide substrates, amorphous carbon, zeolites, aluminosilicates, alkaline earth carbonates such as magnesium carbonate, calcium carbonate or barium carbonate, barium sulphate, montmorillonites, polymer matrices, multifunctional resins, ion exchange resins, ceramic supports or mixtures of two or more of these.

18. The process according to claim 2 carried out in the presence of an organic solvent selected from the group comprising hydrocarbons, esters, ketones, C3-C6 alcohols, and ethers.

19. The process according to claim 3 carried out in the presence of an organic solvent selected from the group comprising hydrocarbons, esters, ketones, C3-C6 alcohols, and ethers.

20. The process according to claim 4 carried out in the presence of an organic solvent selected from the group comprising hydrocarbons, esters, ketones, C3-C6 alcohols, and ethers.

* * * * *